United States Patent

Müller

[11] Patent Number: 6,100,977
[45] Date of Patent: Aug. 8, 2000

[54] DEVICE AND PROCESS FOR MEASURING TWO OPPOSITE SURFACES OF A BODY

[75] Inventor: Dieter Müller, Binzen, Germany

[73] Assignee: Nanopro Luftlager-Produktions-und Messtechnik GmbH, Freiburg, Germany

[21] Appl. No.: 08/930,378
[22] PCT Filed: Aug. 1, 1996
[86] PCT No.: PCT/EP96/03381
  § 371 Date: Sep. 24, 1997
  § 102(e) Date: Sep. 24, 1997
[87] PCT Pub. No.: WO97/27452
  PCT Pub. Date: Jul. 31, 1997

[30] Foreign Application Priority Data

Jan. 24, 1996 [DE] Germany ............... 196 02 445

[51] Int. Cl.[7] ............................................. G01B 9/02
[52] U.S. Cl. ................................. 356/354; 356/356
[58] Field of Search ............................. 356/359, 360

[56] References Cited

U.S. PATENT DOCUMENTS 5,355,221 10/1994 Cohen ................................ 356/359
5,684,594 11/1997 Platten et al. ..................... 356/363
5,889,591 3/1999 Bruning ............................. 356/354

FOREIGN PATENT DOCUMENTS 0 179 935 5/1986 European Pat. Off. .
106 769 7/1974 Germany .
WO 96/22505 7/1996 WIPO .

*Primary Examiner*—Robert H. Kim
*Assistant Examiner*—Andrew H. Lee
*Attorney, Agent, or Firm*—George W. Neuner; Dike, Bronstein, Roberts & Cushman, LLP

[57] ABSTRACT

An apparatus and a method are provided which allow two opposite plane surfaces of a body to be interferometrically measured simultaneously using light from a single light source. From a parallel light beam (P) produced by a light source (1) partial light beams (A, P) having positive and negative diffraction angles are produced using a beam splitter (8) in the form of a diffraction grating. The partial light beams strike the respective surfaces (90, 91) of the body (9) to be measured and are reflected thereat. The reflected partial light beams (A, B) are interfered with the throughgoing partial light beam (P) having an order of diffraction of zero and the thus produced interference patterns are digitized and subtracted from each other, whereby the parallelism of both surfaces (90, 91) of the body can be determined.

30 Claims, 3 Drawing Sheets

DEVICE AND PROCESS FOR MEASURING TWO OPPOSITE SURFACES OF A BODY

The invention relates to an apparatus and a method for measuring two opposite surfaces of a body.

The technical progress of the semiconductor industry in the last years resulted in a sharp increase of the diameters of the semiconductor wafers as base material for chip production for economic and process technical reasons. Wafers having a diameter of 200 millimeters are already state of the art and wafers having a diameter of 300 millimeters will be processed in near future.

At present manufacturers and processors of such wafer sizes do not yet have measuring devices at their disposal which enable them to check particular quality features such as the geometry (flatness, curvature, thickness variation) of the wafer with a desired resolution and precision.

Two measuring methods for measuring the geometry of semiconductor wafers are known. The one measuring method is an optical geometry measurement using interferometry. One entire surface of the wafer is interferometrically measured, while the wafer rests on a plane plate or is sucked thereto. After measuring one surface the wafer is turned around and the other surface is measured. Since, in this method, one side only can be measured at a time, the relation between the front and rear side of the wafer indicating the parallelism and the thickness variation is not directly given. It is assumed that the sucked surface is drawn in an absolutely plane state, but this is practically not the case, because it is prevented by particles between the wafer and the support and it is generally uncertain whether the wafer—especially in case of unevenness—fits in a uniform manner. Furthermore, a horizontally placed wafer having a diameter of 200 millimeters or 300 millimeters is bent by gravity and therefore no forcefree state of the wafer prevails. This renders the measurement of the absolute evenness impossible. Moreover, the risk of damage due to the surface contact with the support and possibly also with the optical measuring system is so high that mostly sample measurements only are admitted. Owing to the sum of the many measuring uncertainties the measuring accuracy is insufficient. Measurement values produced with other methods are not directly comparable also.

A further method is the capacitive geometry measurement including scanning the surface using distance sensors. Dot scanning distance sensors scan the front side and the rear side of a wafer. The wafer is supported at its center and rotated. Since the measurement is punctual, it is necessary to scan in order to obtain two-dimensional data. The known disadvantages of a scanning method, e.g. instable measuring conditions during the entire scanning process, considerably reduce the measuring accuracy. Since the wafer is centrally supported during the measurement, the gravity exerts a strong influence on the form of the wafer by causing a flexion. This influence can be computationally taken into consideration only to an insufficient approximation. Furthermore, the number of measurement points which can be obtained within an acceptable time is too low. The size of the measurement points resulting from the method and from the sensor diameter can not be reduced to an extent necessary to meet the new quality rules. Moreover, the risk of damaging the wafer is high because of the surface contact and of the very small distance of the sensors to the wafer surface for technical reasons. Generally, also in this case the measuring accuracy is too low, owing to the sum of measuring uncertainties. Again, measuring values produced with other methods can not be directly compared.

It is the object of the invention to provide an apparatus and a method for measuring two opposite, substantially plane and parallel surfaces of a body, in particular of a semiconductor wafer, whereby the measuring accuracy can be increased, the damaging risk can be reduced and the measuring time can be decreased.

Further developments of the invention are defined in the subclaims.

The apparatus and the method, resp., has the following advantages:

The front side and the rear side are measured under absolutely equal conditions in a contactless, isochronal and static manner—no wafer movement occurs—and a single sensor is used. No tuning calibration is required. During the measurement the wafer is free of effects from outer forces, because it stands in an upright position. The critical surfaces of the wafer are never touched, and there is therefore a low risk of damage. All required geometry data are derived from a single measurement. Owing to the single measurement the measuring time is considerably reduced, whereby the throughput and the productivity is increased. The measuring accuracy and the resolution in lateral as well as vertical direction are as high as, or even higher than, required by international standards. Moreover, the method detects the wafer in an unaffected state and could therefore form a standard.

Further features and advantages of the invention will be apparent from a description of an embodiment with reference to the Figures.

Figure 1:
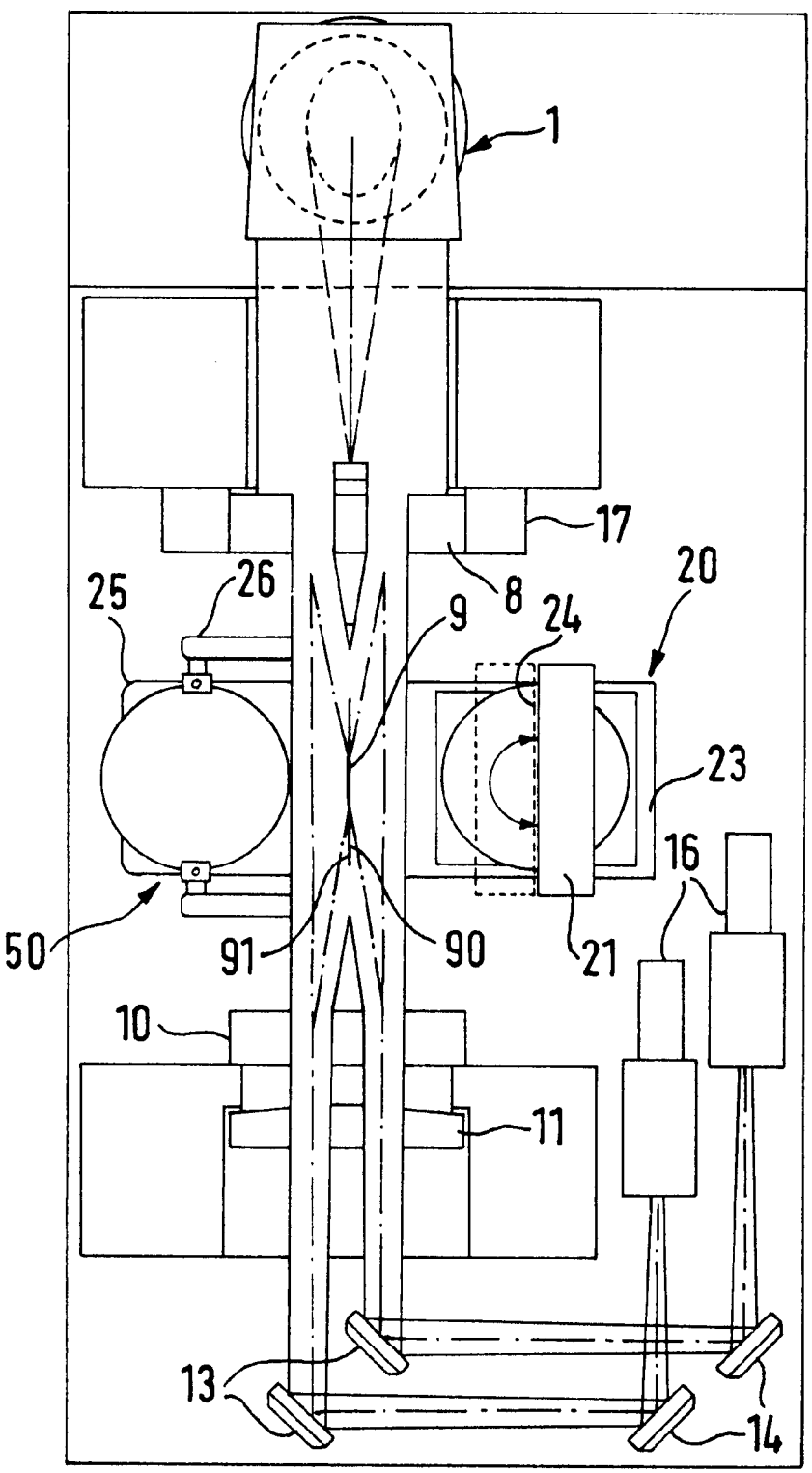
FIG. 1 is a schematic representation of the apparatus.
Figure 2:
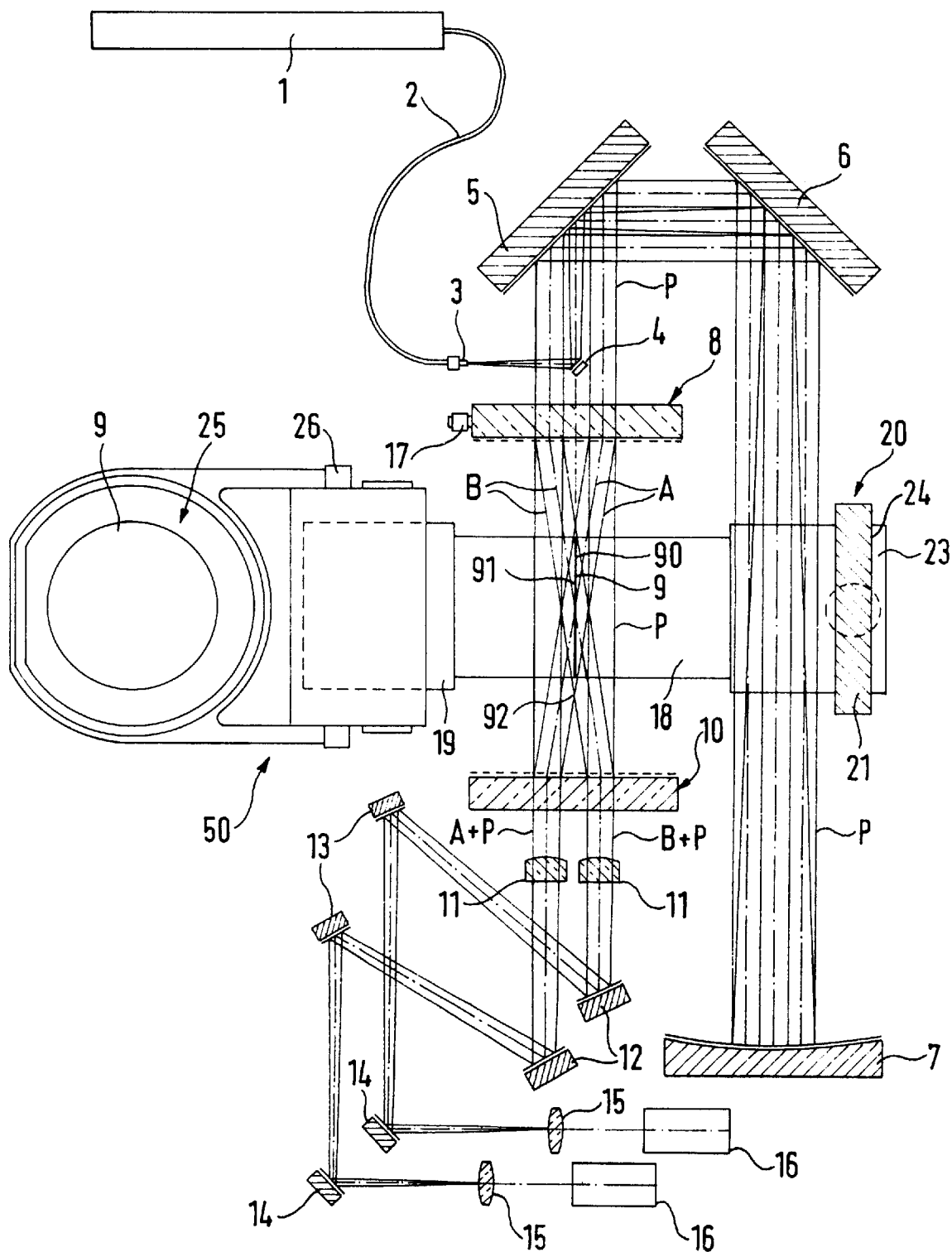
FIG. 2 is a top view of the apparatus showing the path of the rays.

As shown in the FIGS. 1 and 2 the apparatus comprises a light source in the form of a laser 1. The light emitted from the laser 1 is conducted through a beam waveguide 2 to a defined place of the apparatus. The light produced by the laser 1 emerges at an end 3 of the beam waveguides 2 so that the end 3 acts as a punctual light source. The emerging light strikes a deviation mirror 4 wherefrom it is redirected onto a collimation mirror 7 in the form of a parabolic mirror by two further deviation mirrors 5 and 6 which are oriented at an angle of 90° relative to each other. The parallel light beam P reflected from the parabolic mirror 7 reaches a beam splitter 8 through the two deviation mirrors 5 and 6. This beam splitter is formed as a first diffraction grating and is preferably a phase grid. The beam splitter 8 is arranged in the apparatus in a vertical direction and the parallel light beam P strikes the diffraction grating in a perpendicular direction. A beam collector 10 in the form of a second diffraction grating is disposed in a distance from the first diffraction grating and parallel thereto. Behind the beam collector 10 two decollimation lenses 11 are arranged at equal level and the light beams leaving these decollimation lenses are each deflected and focused onto two CCD cameras 16 through deviation mirrors 12, 13, 14 and an optical imaging system 15.

The beam splitter 8 is supported transversely to the optical axis and further comprises a piezoelectric actuating element 17 for shifting the phase of the parallel light beam P by displacing the diffraction grating.

A holding device 50, for example in the form of a support post, is provided centrally between the first diffraction grating and the second diffraction grating. A wafer 9 to be measured is held on the holding device 50 in such a manner that both plane surfaces 90, 91 thereof are arranged in vertical direction parallel to the light beam P. The wafer 9 is supported by the support post substantially at its vertical edge 92 only so that both surfaces 90, 91 are not substantially contacted by the support post and are freely accessible to the interferometric measurement.

Moreover, a receiving device (50, 25) is provided for the wafer 9 to be measured. The wafer can be inserted into the receiving device in a horizontal position. By means of a tilting device 26 the wafer 9 may be tilted from its horizontal position into the vertical measuring position, and the wafer 9 may be transferred, by means of a positionable traveller, into the light path between the first diffraction grating and the second diffraction grating so that the surfaces 90, 91 to be measured are aligned substantially parallel to the undiffracted light beam P and in a substantially vertical direction.

Furthermore, a reference apparatus 20 is provided which comprises a reference body 21 having at least one plane surface 24. The reference body 21 can be introduced into the light path between the first diffraction grating 8 and the second diffraction grating 10 in place of the semiconductor wafer 9 to be measured by means of a traveller 23 with a linear guide 18. The reference body 21 is held so that its plane surface 24 is arranged in vertical direction parallel to the undiffracted light beam P. The reference body 21 can be turned by 180° in its mounting around an axis parallel to its surface 24.

Figure 3:
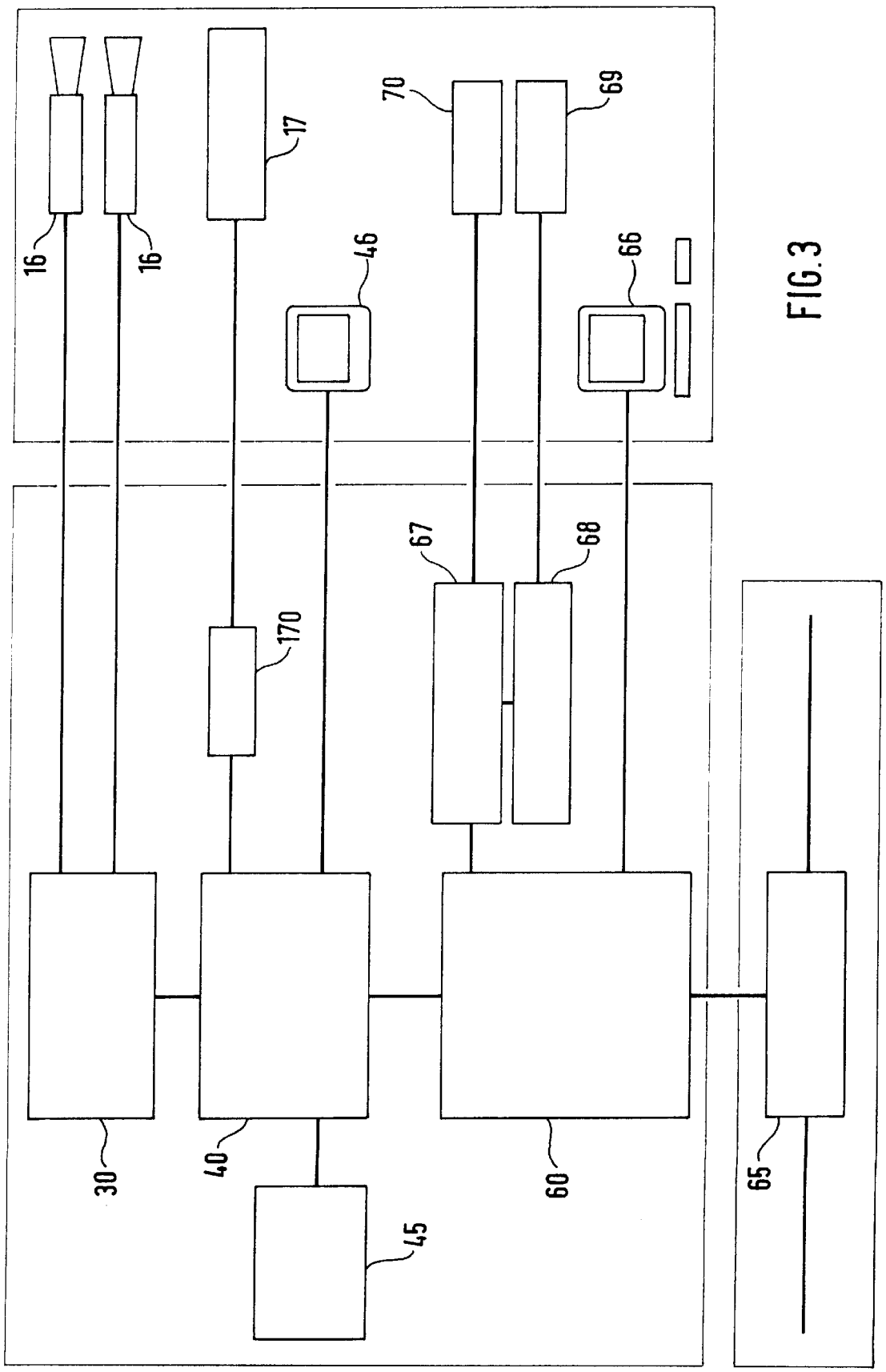
FIG. 3 is a block diagram of the evaluation and operation unit.

As shown in particular in FIG. 3 the apparatus further comprises an electronic device 30 connected to the outputs of the CCD cameras for processing the interference patterns produced by the CCD cameras. The image processing device 30 is further connected to an evaluating processor 40. The evaluating processor 40 is further connected to the phase shifter 17 through a piezo drive member 170. A printer 45 and a video monitor 46 for outputting data are connected to the evaluating processor 40. The evaluating processor 40 is further connected with a master and control unit 60 which is in turn connected with a host computer 65, an operator terminal 66 and the output of an SPC (stored program control) and positioning control. Inputs of the SPC and positioning control are each connected to power electronics 68 for the motors 69 of the travellers for the semiconductor wafer or reference body, resp., to be measured or for moving other mechanical parts of the apparatus. A further input of the SPC and positioning control 67 is connected to the sensor members 70 for the travellers and tilting devices, resp.

In operation the wafer 9 to be measured is first inserted into the wafer receiving device 25. The surfaces 90, 91 to be measured of the wafer 9 are horizontally arranged. By means of the tilting device and of the traveller 19 the wafer to be measured is brought into the holding device 50 where it is arranged so that the surfaces 90, 91 to be measured are vertical. A diffraction of the parallel light beam P striking the first diffraction grating 8 of the beam splitter produces partial light beams A, B, whereby the partial light beam A having a positive diffraction angle strikes the one surface 90 of the wafer and is reflected thereat, whereas the partial light beam B with a negative diffraction angle strikes the other surface 91 of the wafer and is reflected thereat. The 0-th diffraction order of the parallel light beam P passes through the first diffraction grating 8 and is not reflected at the surfaces 90, 91 of the wafer 9. This partial light beam P serves as reference beam for interference with the reflected wave fronts of the beams A and B. In the second diffraction grating 10, the beam collector, the reflected partial light beams A and B, resp., are each combined again with the reference beam P of the 0-th diffraction order and focused, in the form of two partial light beams A+P and B+P, resp., onto the focal planes of the CCD cameras 16 through decollimation lenses 11 and deviation mirrors 12, 13 and 14 as well as positive lenses 15.

During the exposure of the surfaces the phase of the parallel light beam P is repeatedly shifted by 90° and 120°, resp., by displacing the diffraction grating. This produces phase shifted interference patterns. The output data of the CCD cameras 16 are fed to the image processing device 30 which produces digitized phase patterns 160 for each measured surface 90, 91 on the basis of the individual interference patterns of the CCD cameras 16. The digitized phase patterns 160 are further processed in the evaluation processor 40 and imaged on the video monitor 46. The defined shift of the interference phase produced by the phase shifter 17 is evaluated to determine whether there is a protuberance or a depression in the measured surfaces 90, 91. For determining the parallelism of the measured surfaces 90, 91 the two digitized phase patterns are subtracted from each other. Moreover, a mask for the phase patterns is generated in the evaluation processor and the phase patterns are calibrated, parametrized and stored in the evaluation processor. The generated graphics and tables can be outputted via the printer 45.

A calibration using the reference body 21 can be performed before each measurement of a wafer 9. The reference body 21 is introduced into the beam path between the first diffraction grating 8 and the second diffraction grating 10 and the known plane surface 24 is measured. Subsequently the reference body 21 is turned by 180° and the same surface 24 is measured as a second surface.

Modifications of the apparatus and of the method are possible. A body having two precisely plane parallel surfaces may be used for the reference body 21, whereby both surfaces are measured simultaneously. However, the embodiment having a single plane surface of the reference body is more suitable.

What is claimed is:

1. An apparatus for simultaneously measuring two opposite surfaces of a semiconductor wafer, the apparatus comprising:

a light source producing a light beam having a beam path, positioning means for positioning said wafer in said beam path, beam splitter means disposed between said light source and said position of said wafer for splitting said light to form a first partial light beam branched off from said light beam and striking one of said surfaces at an angle to be reflected therefrom, and a second partial light beam branched off from said light beam and striking the other of said surfaces at an angle to be reflected therefrom, holding means for supporting said wafer in a position to expose both surfaces to said partial light beams and to align said surfaces substantially parallel to said light beam, and detector means for producing an interference pattern of said light beam and said reflected partial light beams, thereby determining a thickness variation between the surfaces of the wafer.

2. The apparatus of claim 1, wherein said holding means comprises means for placing said body in said beam path with said surfaces to be measured being substantially vertical.

3. The apparatus of claim 1, wherein said beam splitter means comprises a diffraction grating disposed in said beam path, said first partial light beam comprising waves having a positive diffraction angle and said second partial light beam comprises waves having a negative diffraction angle.

4. The apparatus of claim 1, comprising a calibration device with a reference body having at least one planar surface.

5. The apparatus of claim 4, said calibration device comprising a positioning device for positioning said reference body in said beam path in place of said body to be measured with said planar surface being vertical.

6. The apparatus of claim 5, wherein said positioning device comprises a traveler for positioning said reference body in said beam path.

7. The apparatus of claim 4, wherein said calibration device comprises means for turning said body by 180° around an axis parallel to said planar surface.

8. The apparatus of claim 1, comprising receiving means for receiving said body to be measured in a measurement position whereby said surfaces to be measured are substantially horizontal, and tilting means for tilting said body into said measurement position.

9. The apparatus of claim 1, wherein said detector means comprises two detectors each measuring an interference of a respective one of said partial light beams with said light beam.

10. The apparatus of claim 9, wherein said detectors are formed as CCD cameras.

11. The apparatus of claim 9, comprising an image processing device for producing digitized phase patterns for each of said surfaces from said interference measured from each detector.

12. The apparatus of claim 11, comprising an evaluating means for evaluating said phase patterns.

13. The apparatus of claim 1, comprising a phase shifter for varying the phase of said light beam by a defined amount.

14. The apparatus of claim 1, comprising a beam collector disposed in said beam path between said position of said body and said detector means.

15. The apparatus of claim 14, wherein said beam collector comprises a diffraction grating.

16. The apparatus of claim 1, comprising a parabolic mirror for transforming said light beam produced by said light source into a parallel light beam.

17. The apparatus of claim 1, wherein said light source is a laser.

18. The apparatus of claim 15, comprising a phase shifter for varying the phase of said light beam by a defined amount, wherein said beam splitter means comprises a diffraction grating disposed in said beam path, and wherein said phase shifter comprises a piezoelectric actuating member for displacing said diffraction grating of said beam splitter means.

19. The apparatus of claim 1, comprising a control means for controlling said positioning means for positioning said body and a reference body.

20. A method of simultaneously measuring two opposite surfaces of a semiconductor wafer, said method comprising:

using a single light source to produce a first light beam having a beam path, a second light beam and a third light beam, disposing said wafer in said beam path so that said surfaces are substantially parallel to said first light beam and that said second and third light beams each strike a corresponding one of said surfaces at the same time to be reflected thereat, and producing an interference of said first light beam with each of said reflected second light beam and said reflected third light beam for measuring said surfaces, thereby determining a thickness variation between the surfaces of the wafer.

21. The method of claim 20, comprising disposing said body in said beam path so that said surfaces thereof are substantially vertically aligned.

22. The method of claim 20, comprising producing said first, second and third light beams by splitting a light beam of said light source, using a beam splitter, into three partial light beams, deflecting two of said partial light beams as said second and third light beams onto corresponding ones of said surfaces to be reflected thereat, and using said remaining partial light beam as first light beam to be a reference light beam for the interference measurement.

23. The method of claim 22, comprising producing said second and third partial light beams by diffraction at a grating, using said second light beam, having a positive diffraction angle, for measuring one of said surfaces and using said third partial light beam, having a negative diffraction angle, for measuring the other of said surfaces, and using said first partial light beam, having a diffraction angle of zero, as a reference light beam.

24. The method of claim 20, comprising producing several phase-shifted interference patterns for each surface to be measured.

25. The method of claim 24, comprising digitizing said phase patterns.

26. The method of claim 20, comprising shifting a phase of said partial light beams, using a phase shifting device, by a defined phase angle for producing moving phase patterns for determining protuberances or depressions in said surfaces.

27. The method of claim 24, comprising subtracting said phase-shifted interference patterns of said surfaces from each other for determining a parallelism of said surfaces.

28. The method of claim 20, comprising performing a calibration measurement by bringing a reference body having at least one planar surface into said measurement position and measuring said planar surface.

29. The method of claim 28, comprising turning said reference body by 180° around an axis parallel to said planar surface and again measuring said surface.

30. The method of claim 20, comprising measuring two planar surfaces of a semiconductor wafer.

* * * * *

UNITED STATES PATENT AND TRADEMARK OFFICE

CERTIFICATE OF CORRECTION

PATENT NO.:      6,100,977

DATED:           August 8, 2000

INVENTOR(S):     Dieter Müller

It is certified that error appears in the above-identified patent and that said Letters Patent is hereby corrected as shown below:
    Title page, item
    In the Foreign Application Priority Data section, please correct the priority data as follows:

[30]    Foreign Application Priority Data

GERMANY, JANUARY 24, 1996, 196 02 445.5

Signed and Sealed this

Seventeenth Day of April, 2001

Attest:

NICHOLAS P. GODICI

Attesting Officer        Acting Director of the United States Patent and Trademark Office